United States Patent [19]

Jeffery

[11] Patent Number: 4,929,629

[45] Date of Patent: May 29, 1990

[54] THERAPEUTIC COMPOUND

[75] Inventors: James E. Jeffery, Nottingham, England

[73] Assignee: Boots Company, PLC, Nottingham, England

[21] Appl. No.: 342,638

[22] Filed: Apr. 19, 1989

Related U.S. Application Data

[63] Continuation of Ser. No. 938,395, Dec. 5, 1986, abandoned.

[30] Foreign Application Priority Data

Dec. 17, 1985 [GB] United Kingdom ............... 8531071

[51] Int. Cl.$^5$ ........................................... A61K 31/135
[52] U.S. Cl. ..................................... 514/646; 564/305
[58] Field of Search ......................... 514/646; 564/305

[56] References Cited

U.S. PATENT DOCUMENTS

| 4,443,449 | 4/1984 | Jeffery et al. | 564/305 |
| 4,515,804 | 5/1985 | Marti et al. | 514/456 |
| 4,522,828 | 6/1985 | Jeffery et al. | 564/305 |
| 4,629,727 | 12/1986 | Kozlik et al. | 564/305 |
| 4,746,680 | 5/1988 | Jeffery et al. | 564/305 |
| 4,767,790 | 8/1988 | Jeffery et al. | 564/305 |
| 4,806,570 | 2/1989 | Jeffery et al. | 564/305 |
| 4,814,352 | 3/1989 | Jeffery et al. | 564/305 |
| 4,816,488 | 3/1989 | Rees | 514/646 |
| 4,833,143 | 5/1989 | Armitage et al. | 546/333 |

FOREIGN PATENT DOCUMENTS

| 0089089 | 9/1983 | European Pat. Off. | |
| 0191542 | 8/1986 | European Pat. Off. | |
| 973887 | 10/1964 | United Kingdom | |
| 1530172 | 10/1978 | United Kingdom | |
| 2098602 | 11/1982 | United Kingdom | 514/646 |
| 2127819 | 4/1984 | United Kingdom | |
| 2128991 | 5/1984 | United Kingdom | |

OTHER PUBLICATIONS

Kalir and Pelah, "1-Phenylcycloalkylamine Derivatives II", (1969) pp. 473–477.
Kalir and Karoly, Shirin, et al. "1-Phenylcycloalkylamine Derivatives III", (1975) pp. 125–136.
"Synthesis of New Heterocycles: Part XV–Synthesis of Novel Cyclic and Acyclic Sulphamides", Ind. Jrnl. Chem. vol. 14B, pp. 776–769 (1976), Chem. Abs. 87 23236s.
"Substituted Acetic Acids XXXII–" Army. Khim. Zhurnal, vol. 29, No. 2, pp. 194–199 (1976), Chem. Abs. 85 32678by, (Translation).
Israel J. Chem. 5(5), pp. 223–229 (1967), "1-phenylcycloalkylamine Derivatives I".

Primary Examiner—Glennon H. Hollrah
Assistant Examiner—Amelia A. Owens
Attorney, Agent, or Firm—Neuman, Williams, Anderson & Olson

[57] ABSTRACT

N,N-Dimethyl-1-[1-(4-chlorophenyl)cyclobutyl]-3-methylbutylamine hydrochloride monohydrate is a non-hygroscopic material which can be used as a pharmaceutical in the treatment of depression.

3 Claims, No Drawings

THERAPEUTIC COMPOUND

This application is a continuation of application Ser. No. 938,395, filed Dec. 5, 1986 now abandoned.

The present invention relates to N,N-dimethyl-1-[1-(4-chlorophenyl)cyclobutyl]-3-methylbutylamine hydrochloride which is useful in the treatment of depression.

British Patent Specification 2098602 describes preparative methods which would be suitable for the preparation of the above compound. The present applicants have found that different samples of N,N-dimethyl-1-[1-(4-chlorophenyl)cyclobutyl]-3-methylbutylamine hydrochloride prepared by methods described in the above identified patent application have variable amounts of water contained therein and that these samples are hygroscopic. It is undesirable that hygroscopic materials are used in the preparation of medicines because of the difficulties inherent in the handling of hygroscopic materials. In the preparation of medicines it is essential that a consistent weight of active ingredient is included in each dosage form and it is difficult to achieve such consistency with active ingredients which are absorbing water from the environment. It has now been found that if N,N-dimethyl-1-[1-(4-chlorophenyl)cyclobutyl]-3-methylbutylamine hydrochloride is prepared in the form of a monohydrate a non-hygroscopic product is obtained which is suitable for the preparation of capsules, tablets and other pharmaceutical dosage forms. The present invention therefore comprises N,N-dimethyl-1-[1-(4-chlorophenyl)cyclobutyl]-3-methylbutylamine hydrochloride monohydrate, methods for its preparation, pharmaceutical compositions containing it and the use of those pharmaceutical compositions in the treatment of depression.

N,N-Dimethyl-1-[1-(4-chlorophenyl)cyclobutyl]-3-methylbutylamine hydrochloride monohydrate may be prepared by contacting N,N-dimethyl-1-[1-(4-chlorophenyl)cyclobutyl]-3-methylbutylamine hydrochloride with a medium consisting of or containing water. In a preferred method N,N-dimethyl-1-[1-(4-chlorophenyl)cyclobutyl]-3-methylbutylamine hydrochloride monohydrate is prepared by recrystallising N,N-dimethyl-1-[1-(4-chlorophenyl)cyclobutyl]-3-methylbutylamine hydrochloride from water or a medium containing water, which may be a mixture of water and a water-immiscible solvent (e.g. toluene, xylene or cyclohexane) or a mixture of water and a water-miscible solvent (e.g. acetone, propan-2-ol, industrial methylated spirit, 2-ethoxyethanol, tetrahydrofuran, 1,4-dioxan, methyl acetate or 1,2-dimethoxyethane). Alternative methods to prepare N,N-dimethyl-1-[1-(4-chlorophenyl)cyclobutyl]-3-methylbutylamine hydrochloride monohydrate include (a) contacting solid N,N-dimethyl-1-[1-(4-chlorophenyl)cyclobutyl]-3-methylbutylamine hydrochloride, preferably in finely divided form, with a gaseous medium consisting of or containing water vapour and (b) suspending N,N-dimethyl-1-[1-(4-chlorophenyl)cyclobutyl]-3-methylbutylamine hydrochloride in water or a water-containing medium.

N,N-Dimethyl-1-[1-(4-chlorophenyl)cyclobutyl]-3-methylbutylamine hydrochloride monohydrate may also be prepared by treating N,N-dimethyl-1-[1-(4-chlorophenyl)cyclobutyl]-3-methylbutylamine with hydrochloric acid or a solvent (e.g. acetone or ethanol) containing hydrochloric acid.

The present invention includes pharmaceutical compositions for use in the treatment of depression containing a therapeutically effective amount of N,N-dimethyl-1-[1-(4-chlorophenyl)cyclobutyl]-3-methylbutylamine hydrochloride monohydrate in combination with a pharmaceutically acceptable diluent or carrier. These pharmaceutical compositions may take the form of any of the known pharmaceutical compositions for oral, rectal, parenteral or topical administration. Pharmaceutically acceptable diluents and carriers suitable for use in these compositions are well known in the art of pharmacy. The preferred pharmaceutical compositions are tablets or capsules intended for oral administration. Each tablet or capsule may contain 0.5 to 25 preferably 1 to 12.5 milligrams of N,N-dimethyl-1-[1-(4-chlorophenyl)cyclobutyl]-3-methylbutylamine hydrochloride monohydrate.

The pharmaceutical compositions of the present invention may be used in the treatment of depression in humans. In such treatment a total of 0.5 to 150 preferably 1 to 50 milligrams of N,N-dimethyl-1-[1-(4chlorophenyl)cyclobutyl]-3-methylbutylamine hydrochloride monohydrate may be administered daily in one or more doses.

The invention will now be illustrated by the following Examples which describe the preparation of N,N-dimethyl-1-[1-(4-chlorophenyl)cyclobutyl]-3-methylbutylamine hydrochloride monohydrate. The present applicants have found that N,N-dimethyl-1-[1-(4-chlorophenyl)cyclobutyl]-3-methylbutylamine hydrochloride, which was prepared by methods described in British Patent Specification 2098602 and which is used as the starting material for Examples 1 to 11 and 14 to 16, is hygroscopic and may contain variable amounts, but less than one molar equivalent, of water.

The products of the Examples hereinafter were characterised by satisfactory elemental (C,H,N,Cl) analyses and by satisfactory analysis for their water content.

When attempts are made to determine the melting point of N,N-dimethyl-1-[1-(4-chlorophenyl)cyclobutyl]-3-methylbutylamine hydrochloride monohydrate using conventional laboratory apparatus, it is believed that the sample dehydrates as the temperature is raised and that the melting point observed is that of the dehydrated material.

EXAMPLE 1

N,N-Dimethyl-1-[1-(4-chlorophenyl)cyclobutyl]-3-methylbutylamine hydrochloride (0.5 g) was dissolved in boiling water (5 ml). The solution was filtered whilst hot and the filtrate cooled. The product crystallised from the cooled filtrate and was collected by filtration and dried in vacuo at ambient temperature to give N,N-dimethyl-1-[1-(4-chlorophenyl)cyclobutyl]-3-methylbutylamine hydrochloride monohydrate (m.p. 193°–195.5° C.).

EXAMPLE 2

N,N-Dimethyl-1-[1-(4-chlorophenyl)cyclobutyl]-3-methylbutylamine hydrochloride (5 g) was dissolved in a boiling mixture of toluene (126 ml) and water (12.6 ml). The solution was filtered whilst hot and the filtrate cooled. The product crystallised from the cooled filtrate and was collected by filtration and dried in vacuo at ambient temperature to give N,N-dimethyl-1-[1-(4-chlorophenyl)cyclobutyl]-3-methylbutylamine hydrochloride monohydrate (m.p. 194°–196° C.).

EXAMPLE 3

N,N-Dimethyl-1-[1-(4-chlorophenyl)cyclobutyl]-3-methylbutylamine hydrochloride (10 g) was dissolved in a boiling mixture of acetone (110 ml) and water (1.2 ml). The solution was filtered whilst hot and the volume of the filtrate reduced by the removal by distillation of 80 ml of solvent. The product was collected from the cooled concentrate by filtration and dried in vacuo at ambient temperature to give N,N-dimethyl-1-[1-(4-chlorophenyl)cyclobutyl]-3-methylbutylamine hydrochloride monohydrate (m.p. 195° C.).

EXAMPLES 4 TO 6

A sample (1 g) of N,N-dimethyl-1-[1-(4-chlorophenyl)cyclobutyl]-3-methylbutylamine hydrochloride which had been dehydrated in vacuo at 70° C. for 7 hours was dissolved in a boiling mixture of water (0.5 ml) and an organic solvent (4.5 ml). The solution was allowed to cool to ambient temperature and then stored at 4° C. for three hours. A solid was collected by filtration, washed with the organic solvent and dried in vacuo at ambient temperature for 18 hours to give N,N-dimethyl-1-[1-(4-chlorophenyl)cyclobutyl]-3-methylbutylamine hydrochloride monohydrate the melting point of which is given below.

| Ex. | Solvent | Melting Point °C. |
| --- | --- | --- |
| 4 | industrial methylated spirit | 195–198 (shrinks 160) |
| 5 | propan-2-ol | 195–198 (shrinks 163) |
| 6 | 2-ethoxyethanol | 194–198 (shrinks 166) |

EXAMPLES 7 TO 11

A sample (1 g) of N,N-dimethyl-1-[1-(4-chlorophenyl)cyclobutyl]-3-methylbutylamine hydrochloride which had been dehydrated in vacuo at 70° C. for 7 hours was treated with an organic solvent specified below (x ml) and then water (y ml) was added. The mixture was boiled and the resulting solution allowed to cool to ambient temperature and then stored at 4° C. for three hours. In Examples 10 and 11 the solution was stored at ambient temperature for 18 hours and crystallisation initiated by reducing the volume of the solution under a stream of air. A solid was collected by filtration, washed with the organic solvent and dried in vacuo at ambient temperature for 18 hours to give N,N-dimethyl-1-[1-(4-chlorophenyl)cyclobutyl]-3-methylbutylamine hydrochloride monohydrate the melting point of which is given below.

| Ex. | Solvent | x | y | Melting Point °C. |
| --- | --- | --- | --- | --- |
| 7 | 1,2-dimethoxyethane | 10 | 1 | 196–198 (shrinks 185) |
| 8 | xylene | 15 | 1 | 196–198 (shrinks 166) |
| 9 | cyclohexane | 30 | 2 | 193–197 (shrinks 160) |
| 10 | 1,4-dioxan | 25 | 1 | 196–199 (shrinks 160) |
| 11 | methyl acetate | 25 | 2 | 197–202 |

EXAMPLES 12 AND 13

A sample (1 g) of N,N-dimethyl-1-[1-(4-chlorophenyl)cyclobutyl]-3-methylbutylamine was treated with 5M hydrochloric acid (1 ml) and the mixture was dissolved in the minimum quantity of a boiling organic solvent specified below. The resulting solution was allowed to cool to ambient temperature. A solid was collected by filtration, washed with the organic solvent and dried in vacuo at ambient temperature for 18 hours to give N,N-dimethyl-1-[1-(4-chlorophenyl)cyclobutyl]-3-methylbutylamine hydrochloride monohydrate the melting point of which is given below.

| Ex. | Solvent | Melting Point °C. |
| --- | --- | --- |
| 12 | acetone | 194–197 |
| 13 | ethanol | 196–201 |

EXAMPLE 14

A sample (5 g) of N,N-dimethyl-1-[1-(4-chlorophenyl)cyclobutyl]-3-methylbutylamine hydrochloride was heated with a mixture of toluene (30 ml) and propan-2-ol (3 ml) to 90° C. and allowed to cool to 72° C. Water (0.9 ml) was added and the mixture cooled to 25° C. and then placed in an ice-water bath for 30 minutes. A solid was collected by filtration, washed with cold toluene and dried by suction at ambient temperature to give N,N-dimethyl-1-[1-(4-chlorophenyl)cyclobutyl]-3-methylbutylamine hydrochloride monohydrate [m.p. 193°–195° C. (shrinks 150°–155° C.)].

EXAMPLE 15

A sample (24.1 g) of N,N-dimethyl-1-[1-(4-chlorophenyl)cyclobutyl]-3-methylbutylamine hydrochloride was dissolved in a boiling mixture of water (72 ml) and tetrahydrofuran (7 ml) and the mixture allowed to cool. A solid was collected by filtration and dried at 40° C. to give N,N-dimethyl-1-[1-(4-chlorophenyl)cyclobutyl]-3-methylbutylamine hydrochloride monohydrate (m.p. 193°–195° C.).

EXAMPLE 16

A sample (48.2 g) of N,N-dimethyl-1-[1-(4-chlorophenyl)cyclobutyl]-3-methylbutylamine hydrochloride was suspended and stirred with water (145 ml) for 24 hours at 25° C. The solid was collected by filtration and dried by suction at ambient temperature to give N,N-dimethyl-1-[1-(4-chlorophenyl)cyclobutyl]-3-methylbutylamine hydrochloride monohydrate (m.p. 191°–195.5° C.).

The non-hygroscopic nature of products prepared in the Examples hereinbefore is illustrated by the following comparative experiment. A sample of N,N-dimethyl-1-[1-(4-chlorophenyl)cyclobutyl]-3-methylbutylamine hydrochloride was dehydrated in a vacuum oven at 60° C. for 16 hours and stored in a desiccator over phosphorus pentoxide. Analysis showed that this material contained no water. When the sample was exposed to the atmosphere for one month analysis showed the water content to be approximately 3% corresponding to about 0.6 molar equivalents of water. However, when a sample of N,N-dimethyl-1-[1-(4-chlorophenyl)cyclobutyl]-3-methylbutylamine hydrochloride monohydrate was exposed to the atmosphere for five months there was no increase in water content showing that no absorption of water had occurred.

We claim:

1. An N,N-dimethyl-1-[1-(4-chlorophenyl)cyclobutyl]-3-methylbutylamine hydrochloride monohydrate product in crystalline solid form essentially comprising equimolar amounts of N,N-dimethyl-1-[1-(4-chlorophenyl)cyclobutyl]-3-methylbutylamine hydrochloride and molecularly combined water of hydration, said product exhibiting substantially non-hydroscopic properties when exposed to atmospheric moisture environmental conditions.

2. A pharmaceutical composition comprising an antidepressantly effective amount of the N,N-dimethyl-1-[1-(4-chlorophenyl)cyclobutyl]-3-methylbutylamine hydrochloride monohydrate product of claim 1 in combination with a pharmaceutically acceptable diluent or carrier.

3. A method of treating depression in humans which comprises administering to a human in need thereof an antidepressantly effective amount of the composition of claim 2.

* * * * *